(12) United States Patent
Champreda et al.

(10) Patent No.: US 11,242,507 B2
(45) Date of Patent: Feb. 8, 2022

(54) **MUTANT STRAIN *ASPERGILLUS ACULEATUS* FOR PRODUCING CELLULASE AND XYLANASE AND PREPARATION METHOD THEREOF**

(71) Applicant: PTT Global Chemical Public Company Limited, Bangkok (TH)

(72) Inventors: Verawat Champreda, Bangkok (TH); Surisa Suwannarangsee, Bangkok (TH); Jantima Arnthong, Bangkok (TH); Chatuphon Siamphan, Bangkok (TH); Aphisit Poonsrisawat, Bangkok (TH); Napong Ketsub, Bangkok (TH); Mahattanee Phinyo, Bangkok (TH); Wikanda Techanan, Bangkok (TH); Natthawut Poomsila, Bangkok (TH); Phatthanon Prasitchoke, Bangkok (TH)

(73) Assignee: PTT Global Chemical Public Company Limited, Bangkok (TH)

( * ) Notice: Subject to any disclaimer, the term of this patent is extended or adjusted under 35 U.S.C. 154(b) by 70 days.

(21) Appl. No.: 16/620,258

(22) PCT Filed: May 30, 2018

(86) PCT No.: PCT/TH2018/000029
§ 371 (c)(1),
(2) Date: Dec. 6, 2019

(87) PCT Pub. No.: WO2018/226171
PCT Pub. Date: Dec. 13, 2018

(65) Prior Publication Data
US 2021/0095242 A1    Apr. 1, 2021

(30) Foreign Application Priority Data
Jun. 7, 2017 (TH) .............................. 1701003166

(51) Int. Cl.
| | | |
|---|---|---|
| *C12N 1/14* | (2006.01) |
| *C12P 19/14* | (2006.01) |
| *C12P 21/02* | (2006.01) |
| *C12R 1/66* | (2006.01) |

(52) U.S. Cl.
CPC ............... *C12N 1/14* (2013.01); *C12N 1/145* (2021.05); *C12P 19/14* (2013.01); *C12P 21/02* (2013.01); *C12R 2001/66* (2021.05); *C12Y 302/01004* (2013.01); *C12Y 302/01008* (2013.01)

(58) Field of Classification Search
CPC .............. C12N 1/14; C12Y 302/01004; C12Y 302/01008; C12R 2001/66; C12P 19/14
See application file for complete search history.

(56) References Cited

U.S. PATENT DOCUMENTS

| | | |
|---|---|---|
| 3,734,831 A | 5/1973 | Hulme |
| 6,080,567 A | 6/2000 | Kofod et al. |
| 6,200,797 B1 | 3/2001 | Dunlop et al. |
| 2005/0153397 A1 | 7/2005 | Christensen et al. |

FOREIGN PATENT DOCUMENTS

| | | |
|---|---|---|
| CN | 101942395 A | 1/2011 |

*Primary Examiner* — Maryam Monshipouri
(74) *Attorney, Agent, or Firm* — Troutman Pepper Hamilton Sanders LLP (57) ABSTRACT

The present invention relates to a novel mutant strain *Aspergillus aculeatus* E14-292 and a genetic modification process of said strain, wherein the mutant strain according to this invention can produce cellulase and xylanase more than the BCC199 (wild type). Moreover, the obtained enzymes can be used to digest the pretreatment bagasse to further produce sugars effectively.

20 Claims, 2 Drawing Sheets

MUTANT STRAIN *ASPERGILLUS ACULEATUS* FOR PRODUCING CELLULASE AND XYLANASE AND PREPARATION METHOD THEREOF

TECHNICAL FIELD

Biotechnology relates to a mutant strain *Aspergillus aculeatus* for producing cellulase and xylanase and preparation method thereof.

BACKGROUND OF THE INVENTION

At present, the production of biofuel and basic chemicals from lignocellulosic biomass as substitute of petroleum gains more interests because the effective biorefinery industrials are the integration of fuel, chemicals, materials, and energy from biomass chemical compositions, including their by-products from near-zero waste process to maximize the value of raw materials. This is very interesting way in both technical and economic aspects. Therefore, the saccharification process in the production of biofuel via suitable biological and chemical processes gain more interests.

The lignocellulosic biomass comprises of three main compositions which are cellulose, hemicellulose, and lignin arranging complexly and strongly. Therefore, the pretreatment process of the lignocellulosic biomass is required to break the lignin structure to produce a digestible biomass.

The enzymatic saccharification of biomass is one of the digestion processes that gains many interests in order to produce sugars from biomass in the production of fuel and other biochemical substances because said process requires less extreme chemicals, temperatures, or energy, need no cofactor or other metals in catalyzing. Therefore, many interests have been paid to the enzymatic saccharification of biomass.

The saccharification process uses two main groups of enzyme which are cellulase group and hemicellulase group. The cellulase group comprises of three types of enzyme: 1) endoglucanase, 2) exo-glucanase or cellobiohydrolase, and 3) β-glucosidase, which digests cellulose to glucose. The hemicellulase group comprises of endo-xylanase and β-xylosidase, which digesting xylan which is the main composition of hemicellulose. Moreover, there are other enzymes that digest hemicellulose, such as α-L-arabinofuiranosidase, α-glucuronidase, α-galactosidase, acetyl xylan esterase, ferulicacid esterase, and β-mannanase.

The synergistic action of cellulase and hemicellulase is an important factor in the effective saccharification process. These enzymes can be divided into two main forms: free enzyme and cellulosome containing several enzymes. The cellulosome can be produced from both bacteria and fungi in different genus such as *Clostridium, bacillus, Aeromonas*, or *Trichoderma, Acremonium*, and *Aspergillus*.

At present, there are many methods to improve fungal strains such as induced mutation, recombination, and gene cloning. The chemically induced mutation is one of the popular methods for strain improvement because it is easy and highly effective. There have been several reports and patent documents on the genetic modification of fungi using chemical mutagen for increasing proteins or enzymes production of fungi as the following.

EP 2150615B1 discloses *Acremonium cellulolycus* CF-2612 that can produce cellulase in high amount and the preparation process for cellulase and/or hemicellulase from said strain, including the saccharification method from the obtained enzymes.

WO 2013/028927 A1 discloses the recombinant genetic modification method of trichoderma host cell and polynucleotide of *Aspergillus fumigatus* in order to produce cellulosic enzymes in large amount and to improve the saccharification of biomass.

JP 2016015894A discloses β-glucosidase obtained from mutant strain *Aspergillus aculeatus* with amino acids substitution of nucleotide sequence at gene code 68, 69, 98, 99, 200, 201, 204, 248, 305, 358, 436, 437, and 511.

EP 1479765A3 discloses effective xylanase obtained from the mutant strain *Aspergillus aculeatus* CBS 101.43 by recombinant method for the saccharification of plant cell wall.

JP 2012200184A discloses the preparation of cellulase from mutant strain *Aspergillus aculeatus* by recombination method. Genes related to production of cellulase and hemicellulase were added into wall host of *Aspergillus aculeatus* in order to increase the productivity of proteins, and also JP 2011223962A discloses cellulase produced by the mutant strain *Aspergillus aculeatus* by recombinant method as well.

Nevertheless, one problem of the enzymatic saccharification process is the highly cost of producing enzyme from microbial. There have been attempts to study and develop microbial capable for producing more enzymes. From above-mentioned reason, the microbial capable to produce cellulase and xylanase in abundant amount are required for useful in large scale industry, and applying enzymes for the further production of sugars from agricultural materials.

Moreover, from the information disclosed above, chemically induced genetic modification has not been done with *Aspergillus aculeatus* for producing higher cellulase and xylanase. Therefore, the present invention aims to prepare the mutant strain *Aspergillus aculeatus* from chemical induction which is easy and cheap that makes said strain capable for producing high amount of cellulase and xylanase.

SUMMARY OF INVENTION

This invention relates to a novel mutant strain *Aspergillus aculeatus* E14-292 and a genetic modification process of said fungi, wherein the novel mutant strain is kept at NITE Patent Microorganisms Depositary (NPMD), Japan, under accession number NITE ABP-02391.

The said mutant strain can produce cellulase and xylanase that can be used to digest biomass in order to produce further sugars effectively.

DESCRIPTION OF THE INVENTION

Definitions

Technical terms or scientific terms used herein have definitions as by an ordinary person skilled in the art unless stated otherwise.

Any tools, equipment, methods, or chemicals named here mean tools, equipment, methods, or chemicals being used commonly by an ordinary person skilled in the art unless stated otherwise that they are tools, equipment, methods, or chemicals specific only in this invention.

Use of singular noun or singular pronoun with "comprising" in claims or specification means "one" and including "one or more", "at least one", and "one or more than one".

All compositions and/or methods disclosed and claims in this application aim to cover embodiments from any action, performance, modification, or adjustment without any experiment that significantly different from this invention, and obtain with object with utility and resulted as same as the present embodiment according to an ordinary person ordinary skilled in the art although without specifically stated in claims. Therefore, substitutable or similar object to the present embodiment, including any little modification or adjustment that clearly seen by an ordinary person skilled in the art should be construed as remains in spirit, scope, and concept of invention as appeared in appended claims.

Throughout this application, term "about" means any number that appeared or showed herein that could be varied or deviated from any error of equipment, method, or personal using said equipment or method.

Hereafter, invention embodiments are shown without any purpose to limit any scope of the invention.

The present invention relates to the *Aspergillus aculeatus* E14-292 strain being genetically modified by chemical induction in order to produce novel strain that capable for producing high amount of cellulase and xylanase, including method of genetic modification and the use of obtained enzymes in saccharification of biomass.

*Aspergillus aculeatus* E14-292 according to this invention was kept at NITE Patent Microorganisms Depositary (NPMD) in Japan under the regulations of Budapest Treaty, wherein said strain was deposited on 19 Dec. 2016 under accession number NITE ABP-02391.

Term "culture" used in this invention means including liquid culture or solid culture but not limited to the said methods as long as the strain according to this invention can be cultured.

Term "saccharification" means including the saccharification of cellulose and/or hemicellulose in the biomass to oligosaccharide, disaccharide, monosaccharide, or mixture thereof. In the same way, the saccharification of biomass means including the hydrolysis of glycosidic bond with poly-saccharide by cellulase and/or hemicellulase.

In one embodiment, mutant strain *Aspergillus aculeatus* is obtained from chemically induced genetic modification of *Aspergillus aculeatus* BCC199 (wild type), wherein the said mutant strain is *Aspergillus aculeatus* E14-292.

In one aspect of the invention, the genetic modification process in order to obtain the mutant strain *Aspergillus aculeatus* comprises the following step:

a) contacting the *Aspergillus aculeatus* BCC199 (wild type) to methylethanesulfonate (EMS) at ratio of methylethanesulfonate to fungi in a range of 20-30 mM to $10^7$ spores for 1 to 3 hours;

b) cultivating the mutant strain *Aspergillus aculeatus* obtained from a); and c) isolating the mutant strain *Aspergillus aculeatus* cultivated from step b).

Preferably, the ratio of methylethanesulfonate to the *Aspergillus aculeatus* BCC199 (wild type) is between 25-26 mM to 10 spores for 3 hours.

In one aspect of the invention, the genetic modification process in order to produce the mutant strain *Aspergillus aculeatus* further comprises the adding step of detoxifying agent to remove toxicity of the chemical mutagen, wherein the detoxifying agent is selected from sodium hydroxide or sodium thiosulfate ($Na_2S_2O_3$).

Preferably, the detoxifying agent is sodium thiosulfate ($Na_2S_2O_3$) and is added to reach the final concentration of 3.33% (w/v).

In one aspect of the invention, the culturing process obtained in step b) of the genetic modification process to produce the mutant strain *Aspergillus aculeatus* is operated at the temperature in a range of 20-40° C., preferably 30° C., for 12-24 hours, preferably 20-24 hours.

In one aspect of the invention, the culturing process in step b) can be done in the potato dextrose agar (PDA) containing 4.0 g/L potato starch, 20 g/L dextrose, and 15 g/L agar.

In one aspect of the invention, the isolation of the mutant strain *Aspergillus aculeatus* in step c) can be done by culturing fungi obtained from step b) in solid medium according to Mandels at the temperature in a range of 20-40° C., preferably 30° C. for 100-130 hours, preferably 120 hours. The obtained fungi are dyed with congo red to measure the clear zone and the diameter of colony for the isolation. The mutant strain have higher ratio of diameter of clear zone to the colony than the wild type.

The solid culturing medium according to Mandels containing 0.3 g/L urea, 1.4 g/L diammonium sulfate, 2.0 g/L potassium dihydrogenphosphate, 0.4 g/L calcium chloride, 0.3 g/L magnesium sulfate heptahydrate, 1.0 g/L peptone, 0.2 g/L Tween 80, 5.0 mg/L iron sulfate heptahydrate, 1.6 mg/L manganese monohydrate, 1.4 mg/L zinc sulfate heptahydrate, 2.0 mg/L cobolt chloride hexahydrate, 10 g/L avicel, and 17.5 g/L gelatin.

In one aspect of the invention, preferably, the genetic modification process to produce the mutant strain *Aspergillus aculeatus* is operated twice.

In one aspect of the invention, the mutant strain *Aspergillus aculeatus* E14-292 produced from above-mentioned process have nucleotide sequence of genes related to protein secretion at 1000 base pair before the genes have mutant such as the t-SNARE protein of 3 genes, genes related to the production of Rho type small GTPase 5 genes, and genes related to the production of Rab11/YPT3 small GTPase.

In one aspect of the invention, the production process of cellulase and xylanase from the mutant strain *Aspergillus aculeatus* E14-292 can be performed with fermentation under solid state fermentation (SSF) and submerged fermentation (SmF) conditions.

In one aspect of the invention, the culturing medium for the submerged fermentation is selected from medium containing 35-40 g/L corncob, 10-15 g/L soybean waste, 0.1-0.2 g/L potassium chloride, 0.01-0.04 g/L zinc sulfate heptahydrate, 0.0001-0.0011 g/L nickel chloride hexahydrate, 0.005-0.020 g/L iron sulfate heptahydrate, and 0.5-1.5 g/L Tween 20.

In one aspect of the invention, the culturing medium for the solid state fermentation is selected from medium containing 700-800 g/kg solid medium corncob, 200-300 g/kg solid medium soybean waste, 1-2 g/kg solid medium potassium chloride, 0.05-0.2 g/kg solid medium zinc sulfate heptahydrate, 5-7 mg/kg solid medium nickel chloride hexahydrate, 0.05-0.2 g/kg solid medium iron sulfate heptahydrate, and 5-12 g/kg solid medium Tween 20.

In one aspect of the invention, the solid state fermentation containing the step of cultivating the mutant strain *Aspergillus aculeatus* E14-292 according to claim 1, wherein the ratio of the mutant strain *Aspergillus aculeatus* E14-292 to cultivating medium is in a range of $10^9$-$10^{11}$ spores/kg under the temperature in a range of 25-32° C. for 72-120 hours.

Preferably, the ratio of the mutant strain *Aspergillus aculeatus* E14-292 to cultivating medium is in the range of $1\times10^{10}$-$5\times10^{10}$ spores/kg and operated at the temperature of 30° C. for 96 hours.

In one aspect of the invention, the submerged fermentation process starts from preparing seed inoculum by cultivating the mutant strain *Aspergillus aculeatus* E14-292 in medium, wherein the ratio of the mutant strain *Aspergillus aculeatus* E14-292 to cultivating medium is in a range of $10^7$-$10^9$ spores/L under the temperature in a range of 25-32° C. for 36-60 hours. Then, the obtained seed inoculum is transferred into cultivating medium to reach the concentration of 10-15% (w/v) and fermenting under the temperature in a range of 25-32° C. for 96-144 hours.

Preferably, the seed inoculum preparing step is done by culturing the mutant strain *Aspergillus aculeatus* E14-292 in culturing medium with ratio of the mutant strain *Aspergillus aculeatus* E14-292 to cultivating medium at $1\times10^8$-$5\times10^8$ spores/L at the temperature of 30° C. for 48 hours.

Preferably, the enzyme fermentation step can be done by transferring the seed inoculum into culturing medium until reaching the concentration of in the range of 12-13% (w/v) and fermenting under the temperature of 30° C. for 120 hours.

In one aspect of the invention, the carbon source is selected from cellulose powder or lignocellulosic materials such as rice straw, bagasse, corncob, corn stem. Preferably, the carbon source is corncob.

In one aspect of the invention, fungi can be isolated from culturing medium containing enzymes produced by said fungi by general isolation methods known by an ordinary person skilled in the art such as centrifugation, filtration, or relevant methods. The culturing liquid containing cellulase and xylanase can be used directly as crude enzyme.

In one aspect of the invention, the supernatant containing cellulase and xylanase may be further purified by methods as known by an ordinary person skilled in the art, wherein two or more purification methods may be used together.

In one aspect of the invention, enzymes produced from the mutant strain *Aspergillus aculeatus* E14-292 comprising: 1) cellulolytic enzyme such as cellobiohydrolase, endoglucanase, and β-glucosidase; and 2) hemicellulolytic enzyme such as xylanase, β-xylosidase, α-galactosidase, α-arabinofuranosidase, and pectinesterase.

In one aspect of the invention, enzymes produced from the mutant strain *Aspergillus aculeatus* E14-292 can be used in the saccharification of biomass, wherein the preferable biomass is bagasse.

In one aspect of the invention, the biomass for saccharification may be used in both wet or dry form.

In one aspect of the invention, the biomass for saccharification may be subjected to the pretreatment process selected from: 1) steam explosion using base catalyst method; 2) organic solvent separation method; 3) sodium hydroxide in acetone method; and 4) sodium methoxide in methanol method, or may be the use of two or more pretreatment methods prior to the enzymatic saccharification.

In one aspect of the invention, enzymes produced from the mutant strain *Aspergillus aculeatus* E14-292 can be used together with other enzymes as mixed enzymes or with surfactant in order to increase the saccharification performance of the biomass.

The following parts aim for describing the embodiments of the invention only, not for limiting the scope of this invention in any way.

Example 1: The Genetic Modification of *Aspergillus aculeatus* by Chemical Induction and the Selection of the Mutant Strain that Produce High Amount of Cellulase and Xylanase The *Aspergillus aculeatus* BCC199 (wild type) at the concentration about $1\times10^7$ spores/mL were subjected to chemically induced genetic modification by adding of methylethanesulfonate (EMS) until reaching the final concentration of 25.4 mM and kept of about 3 hours. Then, sodium thiosulfate ($Na_2S_2O_3$) was added until reaching the final concentration of 3.33% (w/v). Then, the mutant strain was cultured in potato dextrose agar (PDA) at the temperature of 30° C. for 24 hours. Then, the obtained strain was isolated for single colony in order to select its strain by culturing in solid medium according to Mandels comprising 0.3 g/L urea, 1.4 g/L diammonium sulfate, 2.0 g/L potassium dihydrogenphosphate, 0.4 g/L calcium chloride, 0.3 g/L magnesium sulfate heptahydrate, 1.0 g/L peptone, 0.2 g/L Tween 80, 5.0 mg/L iron sulfate heptahydrate, 1.6 mg/L manganese monohydrate, 1.4 mg/L zinc sulfate heptahydrate, 2.0 mg/L cobolt chloride hexahydrate, 10 g/L avicel, and 17.5 g/L gelatin. Then, it was incubated at the temperature of 30° C. for 120 hours. The obtained fungi are dyed with congo red and measure the diameter of the clear zone and the colony for the isolation. The mutant strain have higher ratio of diameter of clear zone to the colony than the wild type for further experiments.

Example 2: Physical Characters of the Mutant Strain *Aspergillus aculeatus* E14-292

Figure 1:
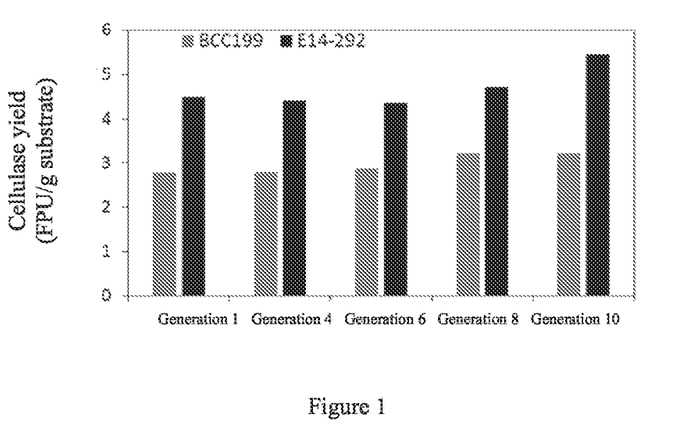
FIG. 1 shows the morphology of the mutant strain *Aspergillus aculeatus* E14-292 comparing with the BCC199 (wild type).

The mutant strain *Aspergillus aculeatus* E14-292 and the wild type were cultured in PDA medium and incubated at the temperature of 30° C. for about 170 hours. The obtained fungi were studied for their morphology using microscope. From FIG. 1, it was found that the mutant strain had smaller colony diameter than the wild type. The diameter of the mutant strain and the wild type were about 27-30 cm and 80-83 cm respectively. Both fungi produced yellowish-gray cleitothecia and brown conidial head arranged in uniseriate. The stripe was smooth and had no wall. The vesicle was oval-round with the size of 27.5-30 microns. The phialide was 10 microns wide and 7.5 microns long. The conidia were round and containing thorns with diameter of 4-7 microns. There was pale yellow sclerotinia with diameter 0.4-0.5 mm.

Example 3: Study of Cellulase and Xylanase Productivity of the Mutant Strain *Aspergillus aculeatus* E14-292

The mutant strain *Aspergillus aculeatus* E14-292 and the wild type were studied for their enzymes productivity by solid state fermentation (SSF) containing corncob and soybean waste at about 700 and 300 g/kg solid medium, respectively. The basic medium contains 20 g/kg solid medium yeast extract, 10 g/kg solid medium potassium hydrogen phosphate, 22 g/kg solid medium disodium hydrogen phosphate, 1.5 g/kg solid medium potassium chloride, and trace elements. The mixture was incubated at the temperature of 30° C. for about 120 hours. The obtained enzymes were kept by adding of 50 mL of 50 mM sodium acetate with pH about 5.0 containing about 0.1% by volume Tween 20. Then, the obtained mixture was shaken at 200 rpm for 60 minutes. The solid part was separated by centrifuge at 9,000 rpm. The separated enzyme solution was subjected the following tests.

1. The total protein concentration was analyzed by Bradford protein assay using BIORAD protein assay and using bovine serum albumin as standard protein solution.

2. FPase was analyzed using 1×6 cm filter paper as substrate and subjected to the reaction under standard conditions (50 mM citrate buffer, pH 4.8, 50° C.). The reducing sugar content was analyzed using dinitrosilicylic acid (DNS) by setting that 1 FPU (filter paper cellulase unit) was equal to the enzyme content that catalyzed 1 µM/min glucose when measured under standard conditions for 60 minutes.

3. Avicelase was analyzed using 1.25% (w/v) avicelase solution as substrate and subjected to the reaction under standard conditions (50 mM citrate buffer, pH 4.8, 50° C.) by setting that 1 enzyme activity unit was equal to the enzyme content that catalyzed 1 µM/min glucose when measured under standard conditions.

4. CMCase and xylanase were analyzed using Carboxymethylcellulose (CMC) as substrate of endoglucanase and 1% (w/v) xylan from beach wood was substrate for xylanase. Said substrate was dissolved in 50 mM Sodium acetate buffer pH 5.0. The reaction was done at the temperature of 50° C. for 10 minutes. Then, the obtained reducing sugar was measured using dinitrosilicylic acid, setting that 1 unit of endoglucase or xylanase was equal to the enzyme content that catalyzed 1 M/min reducing sugar when measured under standard conditions.

5. β-glucosidase and β-xylosidase was analyzed using 5 mM 4-nitrophenyl beta-D-glucopyranoside and 4-nitrophenyl-beta-D-xylopyranoside as substrate of β-glucosidase and β-xylosidase, respectively. The reaction was performed under the condition containing 10 mM sodium acetate buffer pH 5.0 at the temperature of 50° C. for 10 minutes. Sodium carbonate was added to reach the final concentration of 100 mM to stop the reaction. The obtained substance was analyzed for p-nitrophenol at 405 nm, setting that 1 unit of β-glucosidase and β-xylosidase was equal to the enzyme content that catalyzed 1 µM/min p-nitrophenol when measured under standard conditions.

TABLE 1

Cellulase and hemicellulase contents produced from the mutant strain Aspergillus aculeatus E14-292 compared to the wild type

| Enzyme yields | Wild type | Mutant strain Aspergillus aculeatus E14-292 |
| --- | --- | --- |
| protein (mg/mL) | 0.78 ± 0.05 | 1.55 ± 0.06 |
| cellulase (FPU/g substrate) | 3.21 ± 0.20 | 5.46 ± 0.12 |
| avisilase (unit/g substrate) | 0.92 ± 0.02 | 2.13 ± 0.06 |
| endoglucanase (unit/g substrate) | 406.96 ± 17.91 | 732.43 ± 14.47 |
| β-glucosidase (unit/g substrate) | 99.10 ± 3.56 | 287.14 ± 54.21 |
| xylanase (unit/g substrate) | 656.48 ± 14.77 | 1,957.26 ± 8.70 |
| β-xylosidase (unit/g substrate) | 102.45 ± 5.83 | 155.34 ± 24.09 |

Figure 2:
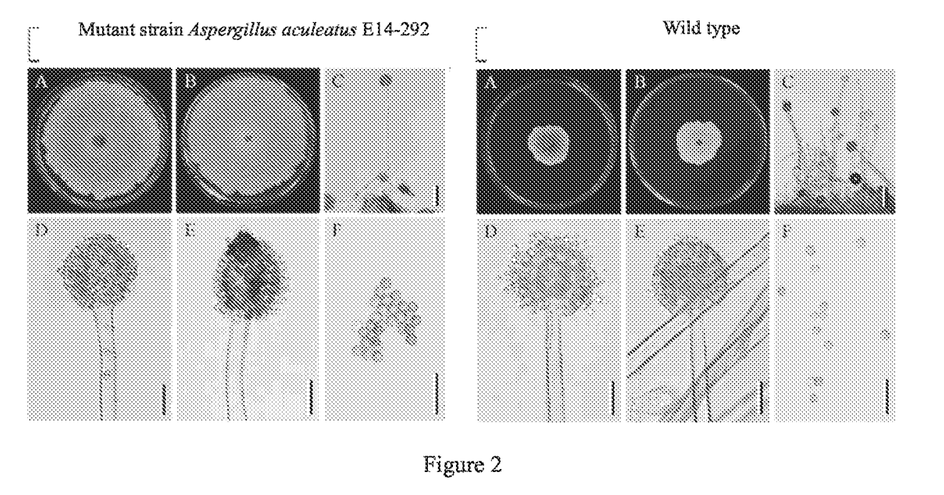
FIG. 2 shows the stability of cellulase and xylanase production by the mutant strain *Aspergillus aculeatus* E14-292 after $10^{th}$ generation.

From table 1, it was found that the mutant strain Aspergillus aculeatus E14-292 had higher cellulase and xylanase production than the wild type Aspergillus aculeatus. Moreover, when tested for enzyme stability of the production, it was found that the mutant strain Aspergillus aculeatus E14-292 had high productivity until $10^{th}$ generation as shown in FIG. 2.

Example 4: Comparison of the Enzyme Production Under Submerged Fermentation and Solid State Fermentation of the Mutant Strain Aspergillus aculeatus E14-292

The enzyme production under submerged fermentation and solid state fermentation was studied to optimize for the economy conditions in enzyme production.

The solid state fermentation (SSF) was done by adding $1 \times 10^{10}$ spores/kg solid medium of Aspergillus aculeatus wild type into flask containing SB1.2 medium comprising 760 g/kg solid medium corncob, 240 g/kg solid medium soybean waste, 1.5 g/kg solid medium potassium chloride, 0.144 g/kg solid medium zinc sulfate heptahydrate, 6 mg/kg solid medium nickel chloride hexahydrate, 0.138 g/kg solid medium iron sulfate heptahydrate, and 10 g/kg solid medium Tween 20. The obtained mixture was adjusted to have initial moisture content of 65% and incubated at the temperature of 30° C. for about 96 hours. The obtained enzymes were kept by adding water or 0.25% by weight Lutensol AO8 solution in the ratio of solid to liquid of 1:10. The obtained mixture was shaken at 200 rpm for 1 hour and centrifuged at 9,000 rpm at the temperature of 4° C. for 5 minutes. The supernatant containing enzymes was separated for further studies.

The submerged fermentation (SmF) was done by preparing seed inoculum by transferring $1 \times 10^{5}$ spores/mL of Aspergillus aculeatus into flask containing 50% SB1.2 medium containing 38 g/L corncob, 12 g/L soybean waste, 0.15 g/L potassium chloride, 0.0144 g/L zinc sulfate heptahydrate, 0.0006 g/L nickel chloride hexahydrate, 0.0138 g/L iron sulfate heptahydrate, and 1 g/L Tween 20. The obtained mixture was incubated at the temperature of 30° C. and shaken at 200 rpm for 48 hours. The obtained seed inoculum was transferred into 50 mL of same medium prepared in flask and shaken at 129 rpm at the temperature of 30° C. for 120 minutes. The obtained enzymes after fermentation were separated by centrifuged at 9,000 rpm at the temperature of 4° C. for 5 minutes. The supernatant containing enzymes was separated for further studies.

Enzymes obtained from liquid (SmF) and solid (SSF) medium were tested for enzyme activity and protein content. The results were shown in table 2.

It was found that under solid state fermentation followed by water or Lutensol A08 solution, the mutant strain Aspergillus aculeatus E14-292 could produce cellulase higher than wild type for about 1.33-1.50 times. Moreover, when analyzing total protein content, it was found that the enzyme solution obtained from the mutant strain Aspergillus aculeatus E14-292 had higher protein content than the wild type for about 1.17-1.29 times.

For submerged fermentation, it was found that the mutant strain Aspergillus aculeatus E14-292 could produce cellulase higher than wild type for about 1.75 times. Moreover, when analyzing total protein content, it was found that the enzyme solution obtained from the mutant strain Aspergillus aculeatus E14-292 had higher protein content than the wild type for about 1.76 times.

These showed that the mutant strain Aspergillus aculeatus E14-292 had a potential in the production of cellulase in higher amount than wild type, and could produce enzymes in both submerged fermentation and solid state fermentation.

TABLE 2

Cellulase and protein yield produced by the mutant strain *Aspergillus aculeatus* EM-292 and BCC199 when cultured under SSF and SmF

| Strain | Fermentation condition | Protein content (mg/mL) | Cellulase yield unit/mL | Cellulase yield unit/g substrate | Cellulase yield unit/mg protein |
|---|---|---|---|---|---|
| mutant strain E14-292 | Solid medium (water) | 1.01 ± 0.03 | 0.48 ± 0.03 | 4.84 ± 0.35 | 0.48 ± 0.03 |
| Wild type | | 0.78 ± 0.02 | 0.32 ± 0.02 | 3.21 ± 0.23 | 0.41 ± 0.03 |
| mutant strain E14-292 | Solid medium (Lutensol) | 1.23 ± 0.07 | 0.52 ± 0.01 | 5.19 ± 0.14 | 0.42 ± 0.01 |
| Wild type | | 1.05 ± 0.01 | 0.39 ± 0.02 | 3.89 ± 0.17 | 0.37 ± 0.02 |
| mutant strain E14-292 | Liquid medium | 0.81 ± 0.04 | 0.49 ± 0.00 | 9.75 ± 0.06 | 0.60 ± 0.00 |
| Wild type | | 0.46 ± 0.06 | 0.28 ± 0.02 | 5.59 ± 0.35 | 0.61 ± 0.04 |

Example 5: Comparison of Nucleotide Sequence of Genetic Materials of the Mutant Strain *Aspergillus aculeatus* E14-292

The comparison of nucleotide sequence of genetic materials of the mutant strain *Aspergillus aculeatus* E14-292 could be done by separation of genetic materials of both fungi by modified CTAB method. Then, about 5 µg of extracted genetic materials were searched for Base sequencing by ion torrent sequencing method using ion personal genome machine (PGM). The obtained base sequencing of wild type and mutant strain *Aspergillus aculeatus* E14-292 were analyzed for their differences by bioinformatics method using information of *Aspergillus aculeatus* ATCC16872 strain as reference genetic materials. The details of different analysis of base sequence in genomes of the mutant strain *Aspergillus aculeatus* E14-292 and wild type were analyzed by bioinformatics method and shown in FIG. 3.

Figure 3:
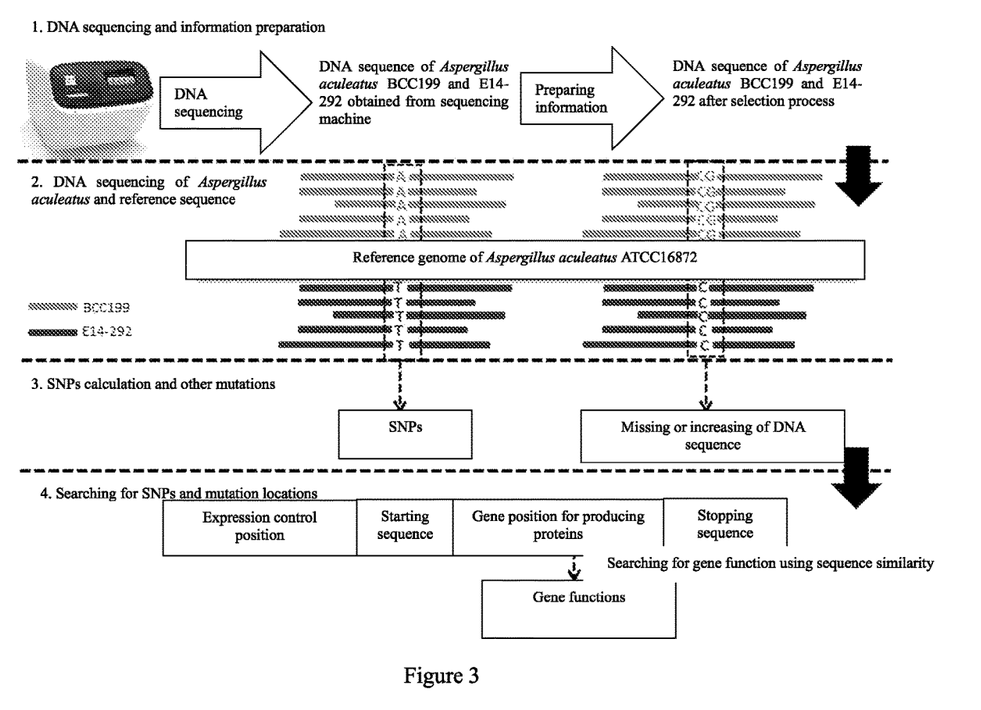
FIG. 3 shows the genetic analysis between the mutant strain *Aspergillus aculeatus* E14-292 and the BCC199 (wild type).

When comparing base sequence of the mutant strain *Aspergillus aculeatus* E14-292 and the wild type, it was found that there were differences in base sequence or mutation gene related to the protein secretion of 24 positions, wherein the differences of base sequence in 1000 base pair before the promoter gene responded for control the expression of gene. This could be counted as 9 genes i.e. 3t-SNARE protein gene (protein code 21025, 43579, 63670), 5 Rho type small GTPase production genes, (protein code 27973, 38545, 42185, 51378, 51654), and 1 Rab11/YPT3 small GTPase production gene (protein code 58898) as shown in table 3, which estimated that might affect the higher secretion of cellulase and hemicellulase. The total protein contents were higher than wild type at 1.76 times.

TABLE 3

Genes related to the production of cellulolytic and xylolytic enzymes and proteins related to transportation of proteins and enzymes outside their cells produced from the mutant strain *Aspergillus aculeatus*

| Mutation area | Gene code | Wild type | Mutant E14-292 | Role of expression proteins |
|---|---|---|---|---|
| 1000 base before gene | 21025 | TAC<br>CAG<br>C | T<br>C<br>CTT | t-SNARE protein |
| | 43579 | T<br>C<br>TA<br>CTTG | TCATTC<br>CTTTA<br>T<br>C | t-SNARE protein SED5/Syntaxin5 |
| | 63670 | G | A | t-SNARE protein |
| | 27973 | G | A | Rho small GTPase protein |
| | 38545 | GA<br>C<br>G | G<br>T<br>GAC | Rho small GTPase protein |
| | 42185 | CA<br>TG<br>C<br>AC<br>AT | C<br>T<br>CA<br>A<br>A | Rho small GTPase protein |
| | 51378 | G<br>AGT<br>A<br>A | GAT<br>A<br>ATT<br>AAGGT | Rho small GTPase protein |
| | 51654 | T<br>A | TG<br>C | Rho small GTPase protein |
| | 58898 | A | AAG | Rab11/YPT3 small GTPase protein |

Example 6: The Use of Enzymes Produced by the Mutant Strain *Aspergillus aculeatus* E14-292 in the Saccharification of Bagasse The conditions for enzymatic saccharification of bagasse was studied in both suitable enzyme content and use of other chemicals such as surfactant, including the type of enzyme production from both submerged fermentation and solid state fermentation.

Five percent (w/v) of pretreated bagasse with steam explosion was added into enzymes produced from the mutant strain *Aspergillus aculeatus* E14-292 until reaching 2.5-20 mg protein/g substrate. Then, phosphate-citrate buffer was added until reaching the concentration of 50 mM, pH 5.0 and sodium azide was added into said mixture until reaching concentration of 0.1%. For the study of surfactant, lutensol surfactant was added into said mixture until reaching the concentration of 0.175% by (v/w) of substrate. The obtained mixture was incubated at the temperature of 45° C. for 72 hours while shaken at 200 rpm. The results were shown in table 4.

TABLE 4

Glucose content obtained from saccharification of bagasse pretreated with steam explosion method at different conditions of enzymes produced by the mutant strain *Aspergillus aculeatus* E14-292 with or without surfactant

| Enzyme content (mg/g) | Reducing sugar content (mg/g substrate) | Glucose content (mg/g substrate) | Xylose content (mg/g substrate) |
|---|---|---|---|
| 2.5 (without surfactant) | 757 | 458 | 212 |
| 2.5 (with surfactant) | 833 | 504 | 229 |
| 5 (without surfactant) | 824 | 532 | 241 |
| 5 (with surfactant) | 889 | 539 | 242 |
| 10 (without surfactant) | 837 | 547 | 266 |
| 10 (with surfactant) | 878 | 566 | 254 |
| 20 (without surfactant) | 824 | 554 | 257 |
| 20 (with surfactant) | 857 | 562 | 300 |

From table 4, it was found that the increasing of enzyme content from 2.5 to 5 mg/g substrate could clearly produce more sugars, and adding of surfactant in the reaction made enzyme produced more sugars.

Moreover, the study of the performance of enzymes produced from submerged fermentation and solid state fermentation was done by adding enzymes produced by the mutant strain *Aspergillus aculeatus* E14-292 to 5% (w/v) pretreated bagasse with steam explosion method until reaching 5-20 mg protein/g substrate. Then, phosphate-citrate buffer was added until reaching the concentration of 50 mM pH5.0. Sodium azide was added into said mixture until reaching the concentration of 0.1%. The obtained mixture was incubated at the temperature of 45° C. for 72 hours while shaken at 200 rpm. The results were shown in table 5.

TABLE 5

Glucose content obtained from the saccharification of bagasse pretreated by steam explosion method of enzymes produced by the mutant strain *Aspergillus aculeatus* E14-292 prepared from submerged fermentation and solid state fermentation at different amounts.

| Enzyme production method | Enzyme content (mg/g) | Reducing sugar content (mg/g substrate) | Glucose content (mg/g substrate) | Xylose content (mg/g substrate) |
|---|---|---|---|---|
| Solid state fermentation | 5 | 941 | 530 | 230 |
| | 10 | 965 | 544 | 239 |
| | 15 | 971 | 544 | 240 |
| | 20 | 1005 | 564 | 250 |
| Submerged fermentation | 5 | 953 | 589 | 241 |
| | 10 | 976 | 568 | 241 |
| | 15 | 1018 | 605 | 261 |
| | 20 | 1012 | 603 | 259 |

From table 5, it was found that sugar content obtained from enzymatic saccharification using submerged fermentation and solid state fermentation were similar. That means enzymes produced from the mutant strain *Aspergillus aculeatus* E14-292 prepared from submerged fermentation and solid state fermentation have a similar efficiency.

Bagasse subjected to different pretreatment methods which were: 1) steam explosion using base catalyst method; 2) organic solvent separation method; 3) sodium hydroxide in acetone method; and 4) sodium methoxide in methanol method were studied for sacchaification started from pretreated bagasse with different methods at 5% (w/v). The bagasse was added by enzymes produced from the mutant strain *Aspergillus aculeatus* E14-292 until reaching 5 mg protein/g substrate. Then, phosphate-citrate buffer was added until reaching the concentration of 50 mM pH 5.0. Sodium azide was added until reaching the concentration of 0.1% into said mixture. Then, lutensol surfactant was added until reaching the concentration of 0.175% (v/w) of substrate into mixture. Then, the mixture was incubated at the temperature of 45° C. for 72 hours while shaken at 200 rpm. The results were shown in table 6.

From table 6, it was found that enzymes produced by the mutant strain *Aspergillus aculeatus* E14-292 could saccharify bagasse subjected to different pretreatment methods effectively.

TABLE 6

Glucose content obtained from bagasse subjected to different pretreatment methods using enzymes produced by the mutant strain *Aspergillus aculeatus* E14-292

| Pretreatment method | Glucose content (mg/g substrate) | Obtained glucose percentage compared with cellulose in substrate | Xylose content (mg/g substrate) |
|---|---|---|---|
| Steam explosion | 559 | 85.7 | 241 |
| Organic solvent separation | 508 | 58.1 | 38 |
| Sodium hydroxide in acetone | 568 | 77.2 | 136 |
| Sodium methoxide in methanol | 531 | 89.2 | 253 |

Effectiveness of enzymes produced from the mutant strain *Aspergillus aculeatus* E14-292 compared with commercial enzymes which were Cellic CTEC 2 (Novozymes, Denmark), Celluclast 1.5 L, (Novozymes, Denmark), and Accelerase 1500 (DuPont, USA) were also used for studying. Bagasse (5% (w/v)) subjected to different pretreatment methods were added with enzymes produced by the mutant strain *Aspergillus aculeatus* E14-292 or commercial enzymes until reaching 5 mg protein/g substrate. Then, phosphate-citrate buffer was added until reaching the concentration of 50 mM pH 5.0. Sodium azide was added until reaching the concentration of 0.1% into said mixture. Lutensol surfactant was added until reaching the concentration of 0.175% by volume per weight of substrate into mixture. Then the mixture was incubated at the temperature of 45° C. for 72 hours while shaken at 200 rpm. The results were shown in table 7.

From table 7, it was found that enzymes produced by the mutant strain *Aspergillus aculeatus* E14-292 could saccharify bagasse subjected to different pretreatment methods effectively which was similar to commercial enzyme Cellic CTEC 2 and better than commercial enzymes Celluclast 1.5 L and Accelerase 1500.

TABLE 7

Effectiveness of enzymes produced by the mutant strain
Aspergillus aculeatus E14-292 compared to commercial
enzymes in saccharification of bagasse pretreated
with steam explosion using base catalyst

| Enzyme | Glucose content (mg/g substrate) | Obtained glucose percentage compared with cellulose in substrate |
|---|---|---|
| Mutant strain Aspergillus aculeatus E14-292 | 559 | 85.7 |
| Cellic CTEC 2 | 586 | 90.0 |
| Celluclast 1.5 L | 267 | 40.9 |
| Accelerase 1500 | 250 | 38.3 |

PREFERRED EMBODIMENT OF THE INVENTION

Preferred embodiment of the invention is as provided in the description of the invention.

The invention claimed is:

1. A fungus strain which is *Aspergillus aculeatus* E14-292, accession number NITE ABP-02391.

2. A genetic modification process to produce the strain *Aspergillus aculeatus* E14-292 according to claim 1, wherein said process comprises the following steps:
   a) contacting the *Aspergillus aculeatus* BCC199 (wild type) with methylethanesulfonate (EMS) at ratio of methylethanesulfonate to fungi in a range of 20-30 mM to $10^7$ spores from 1 to 3 hours;
   b) cultivating the strain *Aspergillus aculeatus* produced from a); and
   c) isolating the strain *Aspergillus aculeatus* E14-292 cultivated from step b).

3. The genetic modification process according to claim 2, wherein in step a) the ratio of methylethanesulfonate to fungi is in a range of 25-26 mM to $10^7$ spores.

4. The genetic modification process according to claim 2, wherein step a) is operated for 3 hours.

5. The genetic modification process according to claim 2, wherein step a) further comprises adding a detoxifying agent selected from sodium hydroxide or sodium thiosulfate.

6. The genetic modification process according to claim 5, wherein the detoxifying agent is sodium thiosulfate ($Na_2S_2O_3$).

7. The genetic modification process according to claim 2, wherein said process steps a), b) and c are operated twice.

8. A production process of cellulase and xylanase by solid state fermentation process comprising the step of cultivating the strain *Aspergillus aculeatus* E14-292 according to claim 1, wherein the ratio of the strain *Aspergillus aculeatus* E14-292 to cultivating medium is in a range of $10^9$-$10^{11}$ spores/kg under the temperature from 25-32° C. for 72-120 hours.

9. The production process of cellulase and xylanase by solid state fermentation process according to claim 8, wherein the ratio of the strain *Aspergillus aculeatus* E14-292 to cultivating medium is in the range of $1\times10^{10}$-$5\times10^{10}$ spores/kg.

10. The production process of cellulase and xylanase by solid state fermentation process according to claim 8, wherein said process is operated at the temperature of 30° C.

11. The production process of cellulase and xylanase by solid state fermentation process according to claim 8, wherein said process is operated for 96 hours.

12. A production process of cellulase and xylanase by submerged fermentation process comprising the following steps:
    a) preparing seed inoculum by cultivating strain *Aspergillus aculeatus* E14-292 in medium, wherein the ratio of the strain *Aspergillus aculeatus* E14-292 to cultivating medium is in the range of $10^7$-$10^9$ spores/L under the temperature from 25-32° C. for 36-60 hours; and
    b) transferring seed inoculum obtained from a) into cultivating medium to reach the concentration of 10-15% (w/v) and fermenting under the temperature from 25-32° C. for 96-144 hours.

13. The production process of cellulase and xylanase by submerged fermentation process according to claim 12, wherein the ratio of the strain *Aspergillus aculeatus* E14-292 to cultivating medium in step a) is in the range of $1\times10^8$-$5\times10^8$ spores/L.

14. The production process of cellulase and xylanase by submerged fermentation process according to claim 12, wherein step a) is operated at the temperature of 30° C.

15. The production process of cellulase and xylanase by submerged fermentation process according to claim 12, wherein step a) is operated for 48 hours.

16. The production process of cellulase and xylanase by submerged fermentation process according to claim 12, wherein the concentration of the seed inoculum in step b) is in the range of 12-13% (w/v).

17. The production process of cellulase and xylanase by submerged fermentation process according to claim 12, wherein step b) is operated in the temperature of 30° C.

18. The production process of cellulase and xylanase by submerged fermentation process according to claim 12, wherein step b) is operated for 120 hours.

19. The production process of cellulase and xylanase by submerged fermentation process according to claim 8, wherein the carbon source is selected from cellulose powder, or lignocellulosic materials selected from rice straw, bagasse, corncob, or corn stem.

20. The production process of cellulase and xylanase by submerged fermentation process according to claim 19, wherein the carbon source is corncob.

* * * * *

UNITED STATES PATENT AND TRADEMARK OFFICE
CERTIFICATE OF CORRECTION

PATENT NO. : 11,242,507 B2
APPLICATION NO. : 16/620258
DATED : February 8, 2022
INVENTOR(S) : Verawat Champreda et al.

Page 1 of 1

It is certified that error appears in the above-identified patent and that said Letters Patent is hereby corrected as shown below:

In the Claims

Column (13); Line (24) replace "ABP-02391" with "BP-02391."

Signed and Sealed this
Twenty-second Day of August, 2023

Katherine Kelly Vidal
*Director of the United States Patent and Trademark Office*